(12) United States Patent
Hsu et al.

(10) Patent No.: US 7,255,705 B2
(45) Date of Patent: Aug. 14, 2007

(54) DISSECTING DEVICE

(75) Inventors: Lih Tao Hsu, Taoyuan (TW);
Wannhsin Chen, Hsin Chu (TW);
Kuang Ning Chang, Taoyuan (TW);
Mei Ju Yang, Hsinchu (TW); Jinn Fa Wu, Taichung (TW); Yeou Bin Guu, Taichung (TW)

(73) Assignee: Industrial Technology Research Institute (TW)

( * ) Notice: Subject to any disclaimer, the term of this patent is extended or adjusted under 35 U.S.C. 154(b) by 544 days.

(21) Appl. No.: 10/743,707

(22) Filed: Dec. 24, 2003

(65) Prior Publication Data

US 2004/0138686 A1 Jul. 15, 2004

(30) Foreign Application Priority Data

Dec. 27, 2002 (TW) .............................. 91137592 A (51) Int. Cl.
*A62B 17/3213* (2006.01)
*B26B 21/00* (2006.01)

(52) U.S. Cl. .............................. 606/167; 30/50; 30/52; 30/304; 30/353

(58) Field of Classification Search ................ 606/167; 30/304, 159
See application file for complete search history.

(56) References Cited

U.S. PATENT DOCUMENTS

| 1,814,528 | A | * | 7/1931 | Purcell | ......................... 30/304 |
| 2,232,321 | A | * | 2/1941 | Gibson | ......................... 30/162 |
| 2,594,932 | A | * | 4/1952 | Judelson | .................. 83/698.11 |
| 4,288,921 | A | * | 9/1981 | Rhynes | ....................... 30/304 |
| 5,456,010 | A | * | 10/1995 | Bryda | ......................... 30/287 |
| 5,680,705 | A | * | 10/1997 | Josoha | ......................... 30/304 |
| 5,713,375 | A | * | 2/1998 | McAllister | .................. 128/898 |
| 5,989,273 | A | * | 11/1999 | Arnold | ....................... 606/167 |

* cited by examiner

*Primary Examiner*—Glenn K. Dawson
(74) *Attorney, Agent, or Firm*—Bacon & Thomas, PLLC (57) ABSTRACT

A device for dissecting an object, such as a cell colony includes a handle and an incision knife module that can dissociate the colony into several colony pieces. In accordance with features of the invention, users can use this dissecting device to cut an object into several pieces quickly and smoothly at a time.

8 Claims, 9 Drawing Sheets

DISSECTING DEVICE

BACKGROUND OF THE INVENTION

1. Field of the Invention

The invention relates to a device for dissecting an object, and more particularly to a device for dissecting a cell colony into at least one colony piece.

2. Description of the Related Arts

A number of recent discoveries have raised expectations that stem cells may be a source of replacement cells and tissue for cells and tissues that are damaged in the course of disease, infection, or because of congenital abnormalities. Various types of putative stem cells differentiate when they divide, maturing into cells that can carry out the unique functions of particular tissues, such as the heart, the liver, or the brain A particularly important discovery has been the development of human embryonic stem (hES) cells (reviewed by R. A. Pedersen, Scientif. Am. 280(4):68, 1999). These cells have the capacity to differentiate into essentially all types of cells in the body. For example, human embryonic stem cells have been used to generate cells that are committed to a number of different cell lineages, which retain their capacity to proliferate. Since these embryonic cells are truly pluripotent, they have the potential to provide a stock supply of different types of cells for regeneration of essentially any type of failed tissue.

The usual method for culturing human embryonic stem cells is to grow them on a layer of embryonic fibroblast feeder cells, such as mouse embryonic fibroblasts.

Human embryonic stem cells are routinely passaged by manual dissociation. Unlike mouse embryonic stem cells, the human cells cannot be enzymatically dispersed into single cells without causing unacceptable levels of death and differentiation. When the colonies reach 1-to-2 mm diameter, they are cut into 5 to 10 pieces with a pulled glass pipette and colony pieces are then re-plated on new feeder layers to proliferate. However, using the pipette to dissociate the colony into several clumps takes a lot of time, resulting in inefficiency. Thus, the dissecting device in accordance with the present invention is designed to overcome the foregoing drawbacks with the prior device.

SUMMARY OF THE INVENTION

It is the object of the present invention to provide a dissecting device which can be used for dissecting an object into several pieces quickly and smoothly at a time.

In one embodiment of the present invention, the device for dissecting an object which comprises: a handle and an incision knife module, formed by at least one set of crossing blades. The incision knife module can form together with said handle.

In anther embodiment of the present invention, the device for dissecting an object which comprises: a handle; a pair of connection apparatuses, coupled with both sides of one end of the handle; an elastic apparatus, coupled with lower side of one end of the handle; and an incision knife module, coupled between the pair of connection apparatuses, said incision knife module comprises at least one knife, and one end of the knife is configured with blades, and the other end of the knife is neighbored to one end of the handle, and facing toward the elastic apparatus.

The blades are integrally formed with one end of the knife. Alternatively, the blades are coupled with one end of the knife through a shaft, and the blades are of roller type.

The incision knife module is coupled between the pair of connection apparatuses through a fixing apparatus, and is deflectable with the fixing apparatus as the axis, and is limited with the deflected displacement through another fixing apparatus.

The handle can be made from any material that can be sterilized, such as alloy, metal, glass, ceramics or plastic. If the selected material is alloy, it is preferably stainless steel.

The blades of knife modules can be made of any material that can be sterilized and is with suitable hardness and pressure resistance for sustaining instant downward pressures, such as, glass, metal, alloy or ceramics. If the selected material is alloy, it is preferably stainless steel.

In accordance with features of the present invention, users can use this device to dissecting an object, such as a cell colony, into several pieces quickly and smoothly at a time. Therefore, it can resolve the drawbacks (such as time-consuming) with the prior device.

BRIEF DESCRIPTION OF THE DRAWINGS

Further objects of the present invention will become apparent from the following description of the invention with reference to the accompanying drawing, in which.

DETAILED DESCRIPTION OF THE INVENTION

Figure 1:
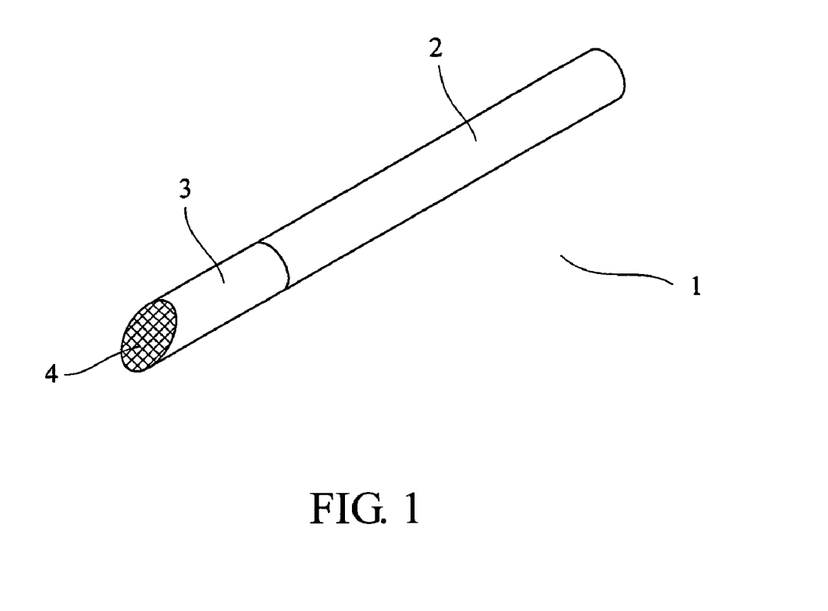
FIG. 1 is a perspective view of the dissecting device for one embodiment according to the present invention.

The device of this invention, as shown in FIG. 1, comprises a handle 2; and, an incision knife module 3, which is composed of a plurality of crossing blades 4, wherein the incision knife module 3 is coupled with the handle 2. The dissecting device 1 is characterized in incising the object into at least one piece at one time, wherein the material for the handle can be made from any material that can be sterilized, such as alloy, metal, glass, ceramics or plastic. The type of the alloy is preferably the stainless steel. The blades 4 of the incision knife module 3 is a material with suitable hardness and pressure resistance for sustaining instant downward pressure, such as glass, metal, alloy or ceramics. The type of the alloy is preferably the stainless steel. The blades 4 of the incision knife module 3 is preferably with the thickness of about 1 µm~100 µm.

Figure 2:
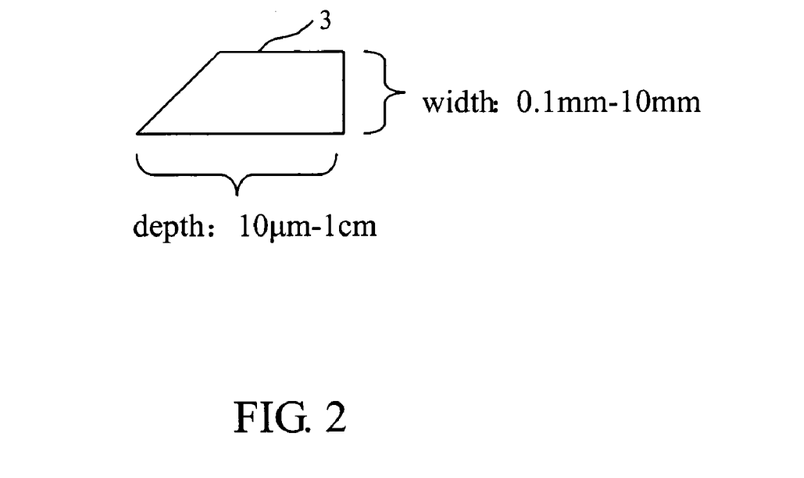
FIG. 2 is a side view of the incision knife module of the dissecting device in FIG. 1.

FIG. 2 shows the side view of the dissecting device 1 provided by the present invention, wherein the incision knife module 3 has the width preferably about 0.1 mm to 10 mm, and the depth about 10 µm to 1 cm.

Figure 3:
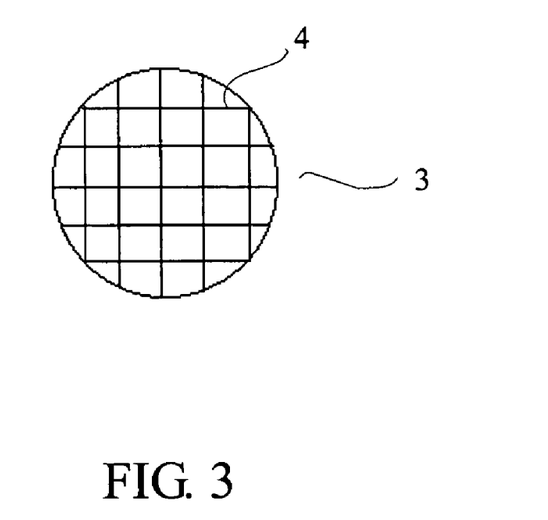
FIG. 3 is a cross-sectional view of the round-shaped incision knife module of the dissecting device in FIG. 1.
Figure 4:
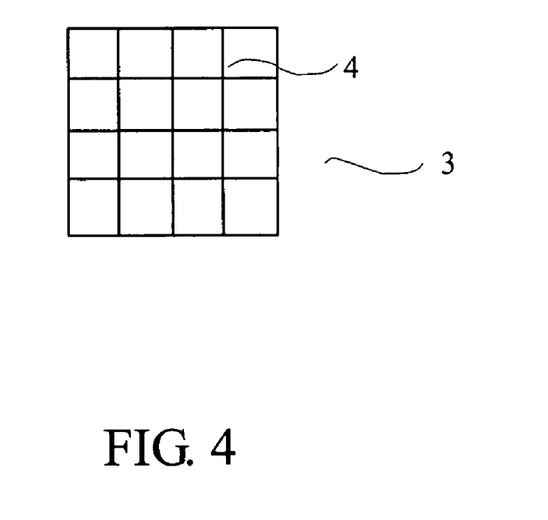
FIG. 4 is a cross-sectional view of the square-shaped incision knife module of the dissecting device in FIG. 1.

FIG. 3 and FIG. 4 show the cross-sections of the incision knife module 3 for the dissecting device according to the present invention. The shape of cross-section has no special limitation, and the shape may be a sphere or square. Moreover, the number of blades and blade pitches for the plurality of crossing blades 4 in the incision knife module 3 can have different alternatives according to the size of original object as well as the size and number of the desired products. Next, please refer to another embodiment of the dissecting device 1 as shown in FIG. 5 to FIG. 8.

Figure 5:
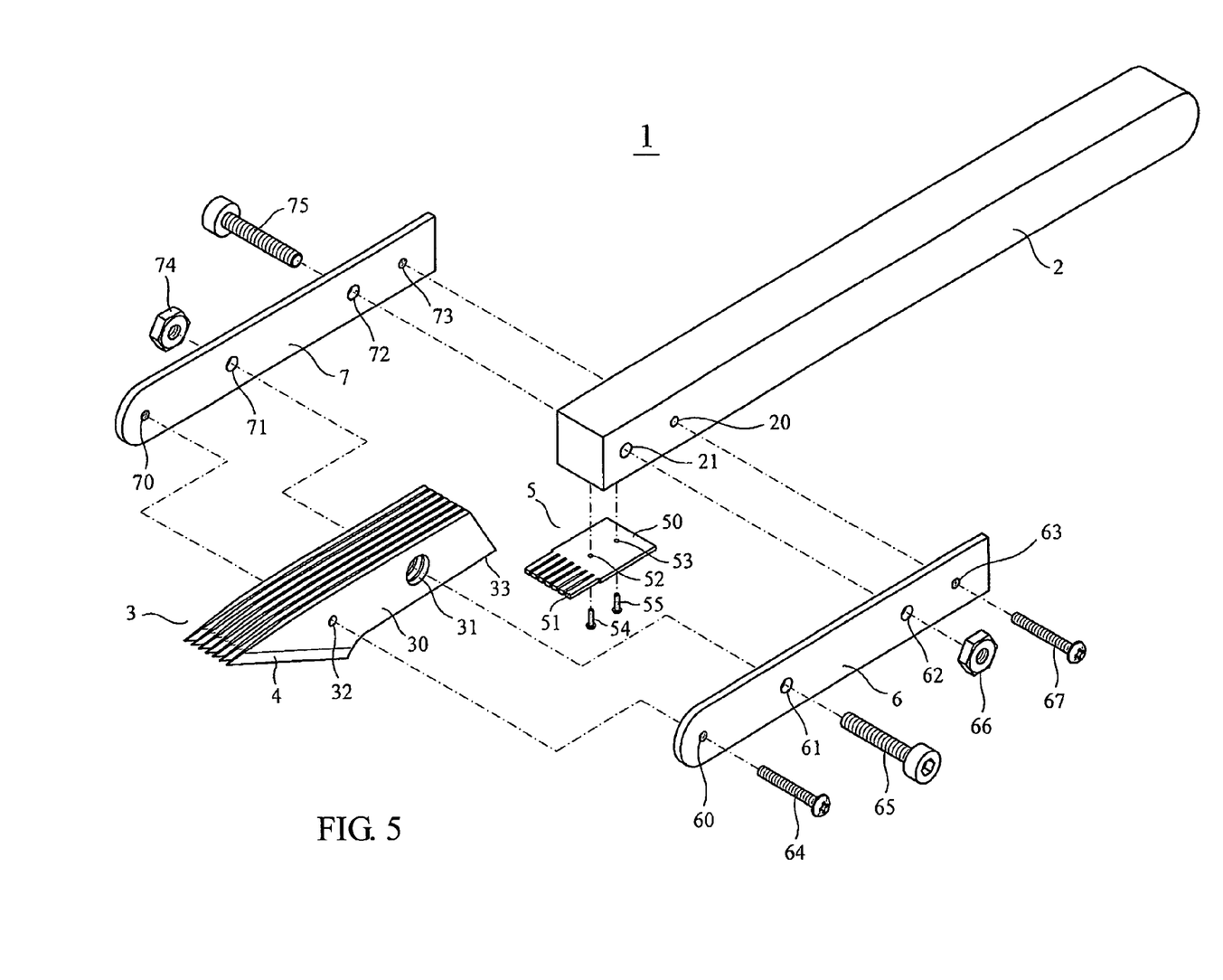
FIG. 5 is an exploded view of the dissecting device for another embodiment according to the present invention.

As shown in FIG. 5, the dissecting device 1 comprises: a handle 2; an incision knife module 3; blades 30 having cutting elements 4; an elastic apparatus 5; the connection apparatuses 6, 7; and, a fixing device. One end of the handle 2 is configured with a pair of through-holes 20, 21 in horizontal arrangement; and, the bottom of the end is configured with a pair of screw holes in vertical arrangement (not shown in the figure). The incision knife module 3 is arranged with a plurality of blades 30 with the same structure, and each blade includes a moving hole 31 and an axial hole 32. The number of the cutting elements 4 is the same as the number of blades 30 of the incision knife module 3, and the cutting elements 4 are integrally formed at the end of each blade 30. The elastic apparatus 5 includes a base 50, and a plurality of leaf springs 51 outwardly extended from one side of the base 50. The neighbored two leaf springs 51 are separated with a gap, and the number of leaf springs 51 is corresponding to the number of the blades 30. The base 50 is configured with a pair of through-holes 52, 53 corresponding to a pair of screw holes not shown in the figure at the bottom of the end of the handle 2. The connection apparatus 6 is configured with a through-hole 60, a through-hole 61, a through-hole 62 and a through-hole 63; wherein the through-hole 60 is corresponding to the axial hole 32 of each blade 30 of the incision knife module 3; the through-hole 61 is corresponding to the moving hole 31 of each blade 30 of the incision knife module 3, but the diameter of the moving hole 31 is larger than that of the through-hole 61; and, the through-holes 62, 63 are corresponding to the through-holes 21, 20 of the handle 2, respectively. The connection apparatus 7 is configured in the opposite of the connection apparatus 6. The connection apparatus 7 is configured with a screw hole 70, a through-hole 71, a through-hole 72 and a screw hole 73; wherein, the screw hole 70 is corresponding to the axial hole 32 of each blade 30 of the incision knife module 3 and the through-hole 60 of the connection apparatus 6; the through-hole 71 is corresponding to the moving hole 31 of each blade 30 of the incision knife module 3 and the through-hole 61 of the connection apparatus 6, but the diameter of the moving hole 31 is larger than that of the through-hole 71; and, the through-holes 72, 73 are corresponding to the through-holes 21, 20 of the handle 2 and the through-holes 62, 63 of the connection apparatus 6. The fixing apparatus is composed of the screws 64, 65, 67, 75, 54, 55, and the screw nuts 66, 74.

The connection apparatuses 6, 7 are located at both sides of the handle 2, and the incision knife module 3 is located between the connection apparatuses 6, 7, and the end 33 of the incision knife module 3 is neighbored to the handle 2, but separated with a suitable pitch. After penetrating the screw 75 sequentially through the through-hole 72 of the connection apparatus 7, the through-hole 21 of the handle 2, and the through-hole 62 of the connection apparatus 6 and screw-fixed with the screw nut 66, and penetrating the screw 67 sequentially through the through-hole 63 of the connection apparatus 6, the through-hole 20 of the handle 2, and locked into the screw hole 73 of the connection apparatus 7, the two connection apparatuses 6, 7 are coupled at one end of the handle 2. Further, by penetrating the screw 64 sequentially through the through-hole 60 of the connection apparatus 6, the axial hole 32 of the incision knife module 3, and locked into the screw hole 70 of the connection apparatus 7, and penetrating the screw 65 sequentially through the through-hole 61 of the connection apparatus 6, the moving hole 31 of the incision knife module 3, and the through-hole 71 of the connection apparatus 7, and screw-locked with the screw nut 74, the incision knife module 3 uses the screw 64 as the axis of deflection, and the screw 65 as the limited deflection displacement, and is held between the two connection apparatuses 6, 7. Moreover, by penetrating the screws 54, 55 through the through-holes 52, 53 of the elastic apparatus 5 and locked into the screw hole of the handle 2 not shown in the figure, the elastic apparatus 5 is fixed at the bottom of one end of the handle 2. Then, the dissecting device 1 is thus composed, and the side view, the top view and the upward view are referred to FIG. 6 to FIG. 8.

Figure 6:
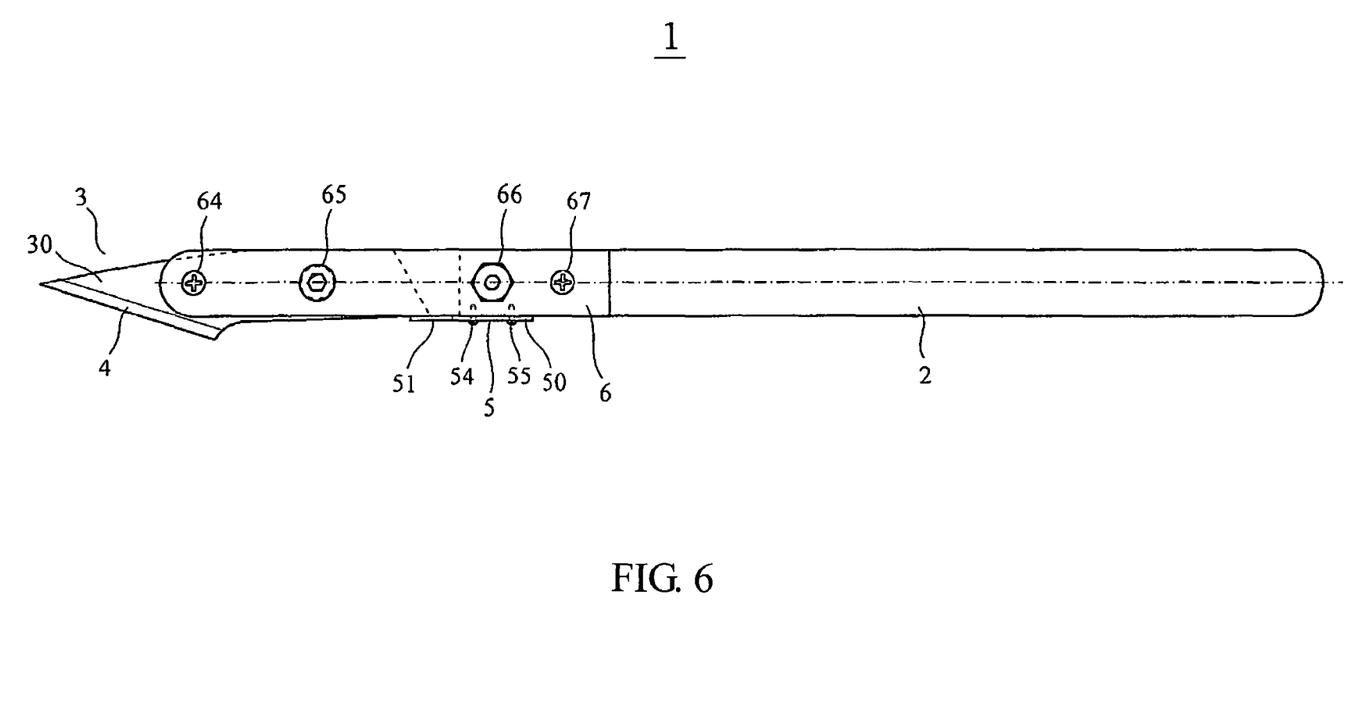
FIG. 6 is a side view of the dissecting device in FIG. 5.
Figure 7:
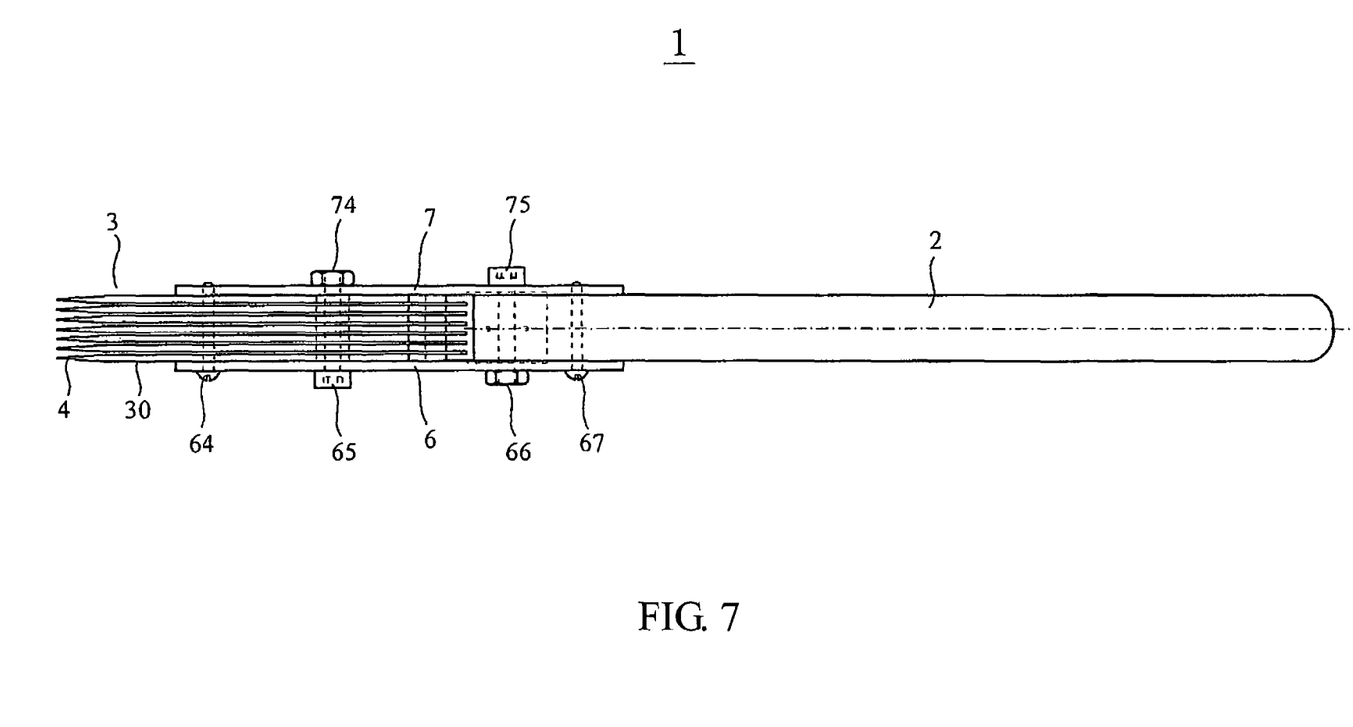
FIG. 7 is a top view of the dissecting device in FIG. 5.
Figure 8:
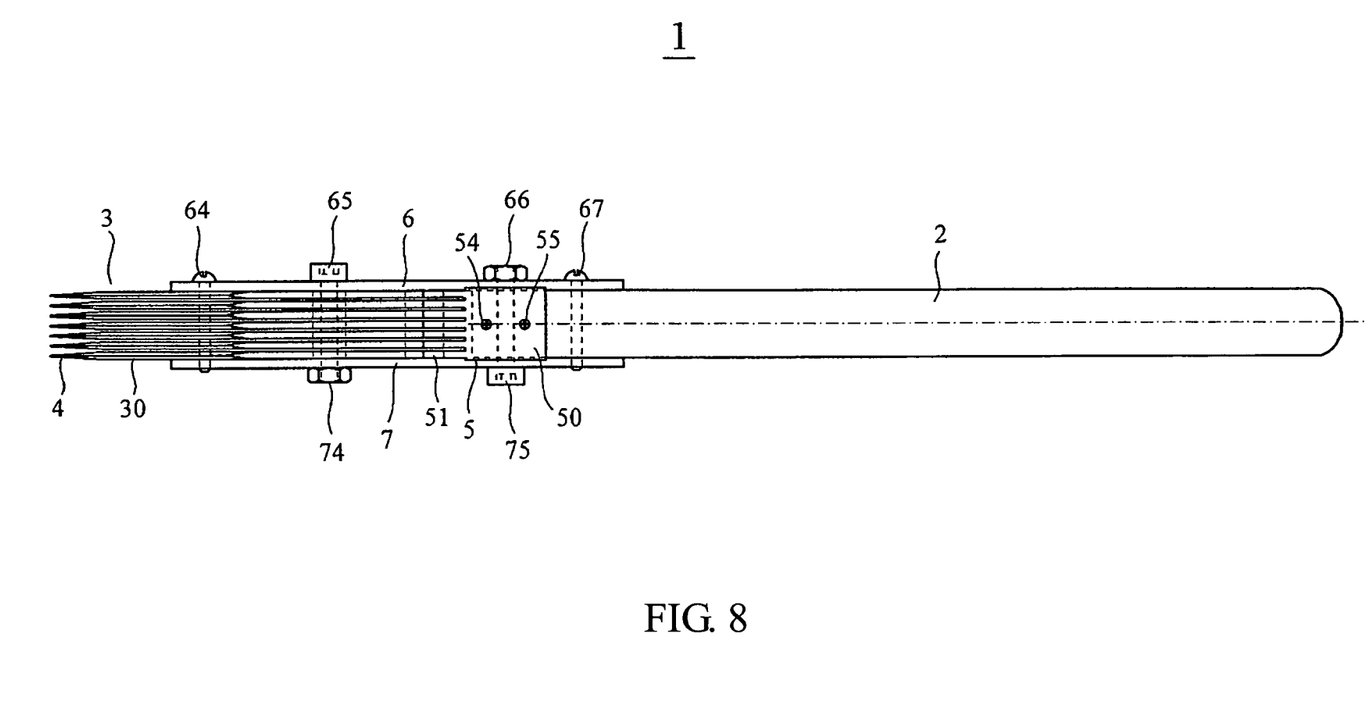
FIG. 8 is a bottom view of the dissecting device in FIG. 5.

Under the horizontal arrangement state as shown in FIG. 6, the incision knife module 3 of the dissecting device 1 has the axis (screw 64) configured deflected to the left, so the center of gravity of the incision knife module 3 is deflected to the right, causing the bottom of the right end 33 (as shown in FIG. 5) facing the leaf spring 51 against the leaf spring 51. In other words, each leaf spring 51 of the elastic apparatus 5 is carried with the right end 33 of each blade 30 of the incision knife module 3, with the functions described below.

Figure 9:
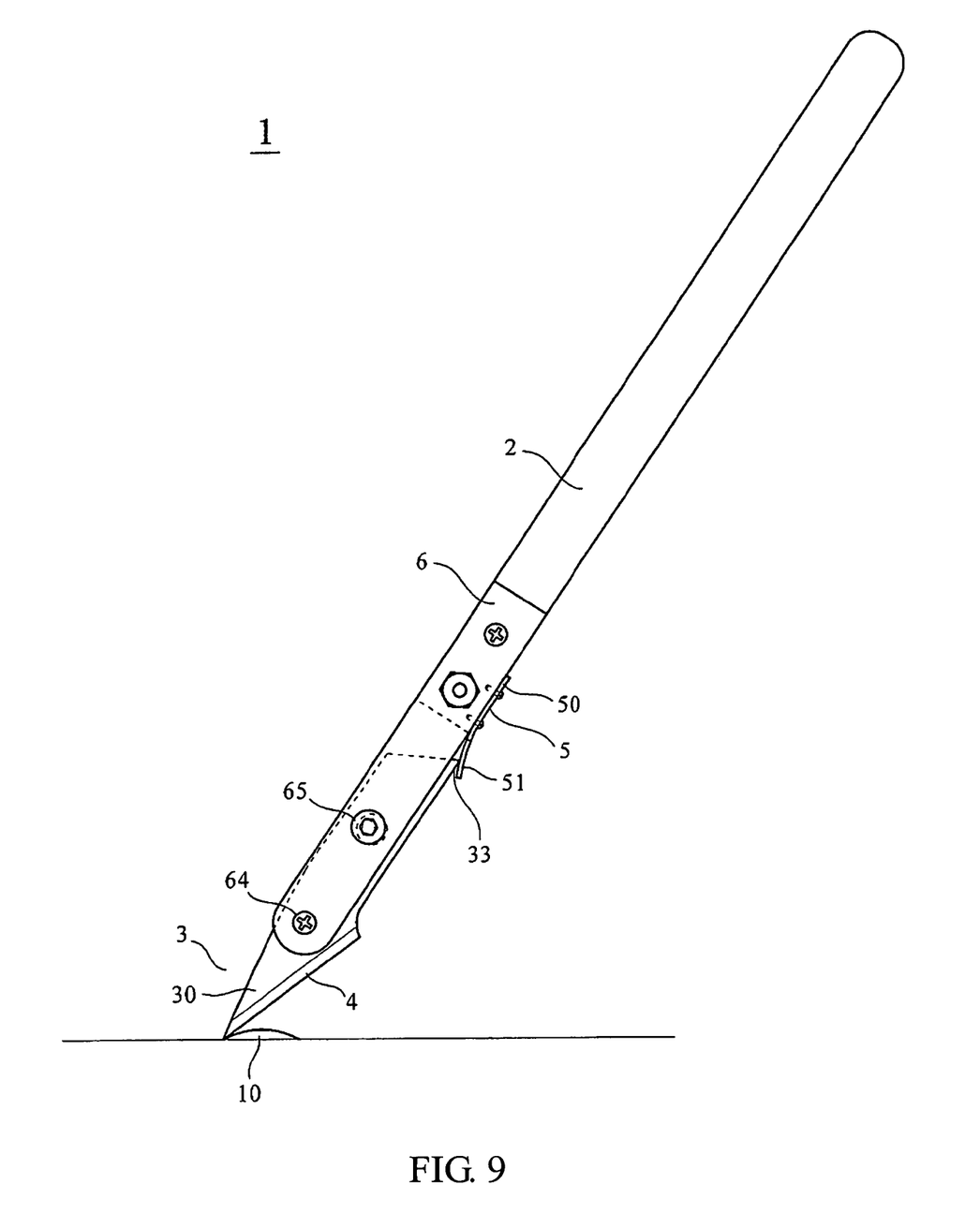
FIG. 9 is a side view of the dissecting device in FIG. 5 under the operation state.

Referred to FIG. 9, when the operator carries the dissecting device 1 to incise the object 10 on the working table, the focus point of the operator's hand is located on the connection apparatuses 6, 7 and the handle 2 of the dissecting device 1, wherein the cutting elements 4 of the dissecting device 1 are the forcing point, and the incision knife module 3 is deflected in clockwise direction with the screw 64 as the axis. Now, the incision knife module 3 can be deflected with a certain stroke by having the diameter of the moving hole 31 larger than the screw 65, so that the right end 33 of the incision knife module 3 after deflection is deflected downwardly to press the leaf spring 51 of the elastic apparatus 5 for elastic deformation and elastic force storage. Because each blade 30 of the incision knife module 3 is independent, and pressed onto the corresponding leaf spring 51, when incising the object 10, the one-step operation can obtain a plurality of pieces. Also, each blade 30 can press against a leaf spring 51 to absorb the deflection generated by incising the object 10 on the ragged surface, so that the incising process can be neat and tidy for obtaining the object with smooth cuts.

Figure 10:
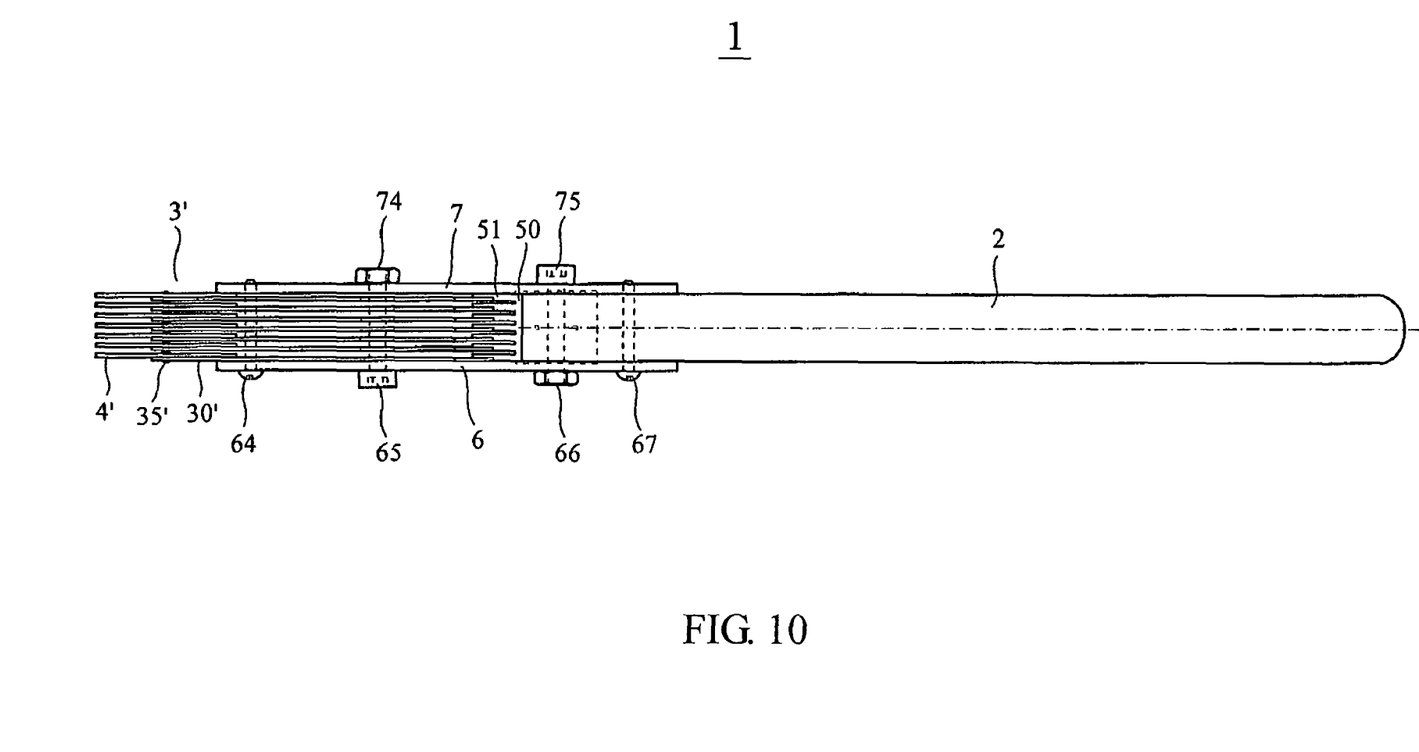
FIG. 10 is a side view of the dissecting device for a further embodiment according to the present invention.
Figure 11:
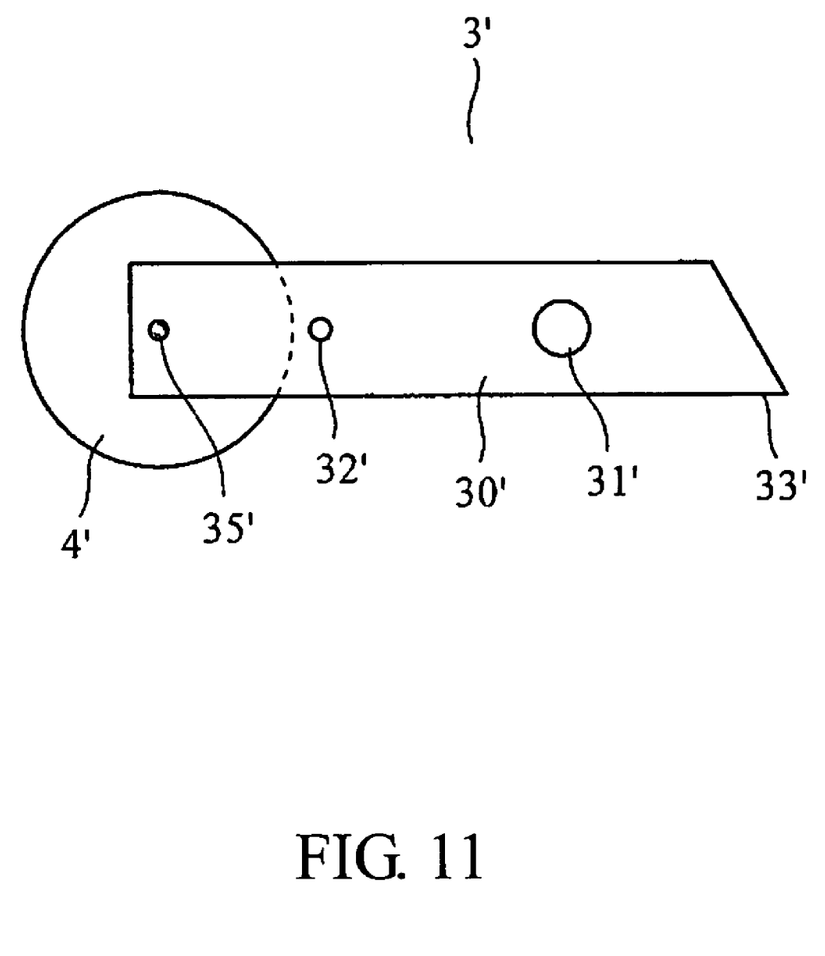
FIG. 11 is a side view of the incision knife module of the dissecting device in FIG. 10.

Next, referred to another embodiment shown in FIG. 10 and FIG. 11, the difference of the embodiment to the embodiment shown in FIG. 5 is: the left end opposite to the right end 33' of each blade 30' of the incision knife module 3' as shown in FIG. 10 and FIG. 11 uses another shaft 35' coupling with roller-type of cutting elements 4'. With this configuration, the cutting elements 4' uses the shaft 35' as the rotation axis, and incises the object in a rolling manner during the incising process. And, each blade 30' can press against a leaf spring 51 to absorb the deflection generated by incising the object on the ragged surface, so that the incising process can be neat and tidy for obtaining the object with smooth cuts. Because the other structures and functions of the embodiment shown in FIG. 10 and FIG. 11 are identical with the embodiment in FIG. 5, it will not be further described.

The connection apparatuses 6, 7 and/or the elastic apparatus 5 can be made with the handle 2 in an integrated manner, and the screw holes 70, 73 of the connection apparatus 7 need not to be threaded, and only form with through-holes, and further with screw nuts associated with the penetrated screws 64, 67 to lock these screws. For all these criteria, the present invention will not strictly limit with.

In accordance with features of the present invention, such device can be adapted to dissect a cell colony into several clumps be passaged during cell culture, and particularly human embryonic stem cell culture.

EXAMPLES

Example 1

This example utilizes the dissecting device 1 as shown in FIG. 1 including a handle 2 that is made from stainless steel and an incision knife module 3 having 3 mm thickness and 5 mm depth. This incision knife module comprises crossing blades 4 that are made from stainless steel of 10 μm in thickness. This device can be sterilized by placing it in an autoclave that runs for 20 minutes at 121° C. in temperature and 15 Psi in pressure.

FIG. 2 is a side view of the dissecting device 1 of the present invention. The preferred width for knife module 3 should be about 0.1 mm to 10 mm, and the preferred depth should be about 10 μm to 1 cm.

FIGS. 3 and 4 show the cross-sectional views of incision knife module 3 of the dissecting device 1. There are no restrictions in the shape of the incision knife module 3 of this invention. For example, the device can be circular or square in shape. Also, one can adjust or select the numbers of and distances between the crossing blades 4 according to the size of original cell colony as well as the size and number of the desired colony pieces.

Using the invented dissecting device, one can quickly incise a cell colony, according to the desired shape without using viewing tools such as microscopes or dissecting microscopes.

Example 2

Alternatively, the handle is made from plastic and the blades are made from glass. All other steps are the same as the example 1.

As far as using the invented device for incising a cell colony, one may control the handle to cause soft pressing of the device on the cell colony from top to bottom, similar to pressing a stamp. This soft pressing results in cutting the cell colony into at least one or more colony pieces. One may adjust the device's depth and thickness as well as the number of and distances between blades, in order to change the number and size of the desired products.

Accordingly, in the present invention, the dissecting device shown in FIG. 5 to FIG. 8, and the dissecting device shown in FIG. 10 to FIG. 11, they are both treated in a high-temperature and high-pressure sterilizing autoclave according to a conventional sterilizing procedure (normally, in high temperature of 121° C., in vapor pressure of 15 Psi, in 20-minute sterilization) and then ready to be used; and, the handle can choose the stainless steel material or the plastic material, and the blade can choose the glass material or the stainless steel material.

The invention described above allows quick incision of cell colonies, quite suitable for experiments that require incision of cell colonies. For example, when one wants to incise a colony of embryonic stem cells to passage using invented device, there would be no need for microscopes. As a result, one can cut the colony into many colony pieces at a time, making this invention valuable.

Although the present invention has been described in considerable detail with reference to certain preferred embodiments thereof, those skilled in the art can easily understand that all kinds of alterations and changes can be made within the spirit and scope of the appended claims. Therefore, the spirit and scope of the appended claims should not be limited to the description of the preferred embodiments contained herein.

What is claimed is:

1. A device for dissecting an object, comprises:
   a handle;
   a pair of connection apparatuses, coupled with both sides of one end of the handle;
   an elastic apparatus, coupled with lower side of one end of the handle, said elastic apparatus having a base and a plurality of leaf springs outwardly extended from one side of said base, each said leaf spring being independently flexible; and
   an incision knife module, coupled between the pair of connection apparatuses,
   wherein said incision knife module comprises at least one blade having a first end having a cutting element and a second end adjacent to one end of the handle, and facing toward the elastic apparatus, wherein the second end of each said at least one blade corresponds to a respective one of said leaf springs.

2. The device according to claim 1, wherein the pair of connection apparatuses are integrally formed with the handle.

3. The device according to claim 1, wherein the pair of connection apparatuses are coupled at both sides of one end of the handle with at least one fixing device.

4. The device according to claim 1, wherein said cutting element is integrally formed with the first end of said at least one blade.

5. The device according to claim 1, wherein the incision knife module is coupled between the pair of connection apparatuses through a fixing apparatus, and is deflectable with the fixing apparatus as the axis, and is limited with the deflected displacement through another fixing apparatus.

6. The device according to claim 1, wherein the elastic apparatus is integrally formed with the handle.

7. The device according to claim 1, wherein the elastic apparatus is coupled at the lower side of one end of the handle through at least one fixing apparatus.

8. The device according to claim 1, wherein said object is a cell colony.

* * * * *